United States Patent [19]

Mallen

[11] Patent Number: 5,540,964
[45] Date of Patent: Jul. 30, 1996

[54] MOISTURE TRANSPORT CAST LINING MATERIAL FOR USE BENEATH AN ORTHOPEDIC CAST, BEING IN THE FORM OF A FABRIC AND CONSISTING ESSENTIALLY OF SYNTHETIC HYDROPHOBIC FIBERS OR A BLEND OF SYNTHETIC HYDROPHOBIC FIBERS AND A SECOND DIFFERENT FIBER

[75] Inventor: Ted A. Mallen, Chattanooga, Tenn.

[73] Assignee: Intera Technologies, Inc., Cleveland, Tenn.

[21] Appl. No.: 305,608

[22] Filed: Sep. 14, 1994

Related U.S. Application Data

[63] Continuation-in-part of Ser. No. 217,849, Mar. 25, 1994, abandoned.

[51] Int. Cl.$^6$ .............................. B29D 22/00; B32B 5/06; A61F 5/00; A61F 13/00
[52] U.S. Cl. ..................... 428/36.1; 428/36.9; 428/219; 428/220; 428/229; 428/231; 428/245; 428/288; 428/297; 428/303; 602/1; 602/900
[58] Field of Search ................................. 428/36.1, 245, 428/229, 288, 36.9, 219, 220, 230, 231, 297, 303; 602/1, 3, 41, 60, 900

[56] References Cited

U.S. PATENT DOCUMENTS

| | | |
|---|---|---|
| 2,858,830 | 11/1958 | Robins . |
| 3,652,212 | 3/1972 | Machell . |
| 4,002,737 | 1/1977 | Borris . |
| 4,081,381 | 3/1978 | Rosenmund et al. . |
| 4,242,408 | 12/1980 | Evani et al. . |
| 4,448,839 | 5/1984 | Morris . |
| 4,516,572 | 5/1985 | Schlein . |
| 4,539,982 | 9/1985 | Bailly . |
| 4,554,317 | 11/1985 | Behar et al. . |
| 4,563,507 | 1/1986 | Dyer . |
| 4,672,005 | 6/1987 | Dyer . |
| 4,705,831 | 11/1987 | Dyer . |
| 4,726,968 | 2/1988 | Hayashi . |
| 4,743,267 | 5/1988 | Dyer . |
| 4,790,907 | 12/1988 | Mallen . |
| 4,806,125 | 2/1989 | Dyer . |
| 4,808,188 | 2/1989 | Ledford et al. . |
| 4,921,890 | 5/1990 | Hayashi . |
| 5,016,622 | 5/1991 | Norvell . |
| 5,098,500 | 3/1992 | Reed et al. . |
| 5,102,711 | 4/1992 | Keller et al. . |
| 5,154,727 | 10/1992 | Dyer . |
| 5,277,954 | 1/1994 | Carpenter et al. . |
| 5,288,544 | 2/1994 | Mallen . |

FOREIGN PATENT DOCUMENTS

| | | |
|---|---|---|
| 1210905 | 12/1982 | Canada . |
| 1241157 | 6/1983 | Canada . |

*Primary Examiner*—James D. Withers
*Attorney, Agent, or Firm*—Oblon, Spivak, McClelland, Maier & Neustadt, P.C.

[57] ABSTRACT

A cast lining fabric is prepared from hydrophilic synthetic material. The cast lining transports moisture from the skin and environment beneath a cast to the outside environment where the moisture is removed by evaporation providing a dry atmosphere beneath the cast. The resulting dry environment reduces the ill effects of bacterial, fungal and mildew growth, reduces odor, increases dryness and comfort, and allows the wearer to bathe and swim.

25 Claims, 2 Drawing Sheets

MOISTURE TRANSPORT CAST LINING MATERIAL FOR USE BENEATH AN ORTHOPEDIC CAST, BEING IN THE FORM OF A FABRIC AND CONSISTING ESSENTIALLY OF SYNTHETIC HYDROPHOBIC FIBERS OR A BLEND OF SYNTHETIC HYDROPHOBIC FIBERS AND A SECOND DIFFERENT FIBER

This application is a continuation-in-part of U.S. application Ser. No. 08/217,849 filed Mar. 25, 1994, now abandoned.

FIELD OF THE INVENTION

The present invention relates to a cast lining material prepared from a moisture transporting synthetic fiber fabric. The cast lining of the invention transports moisture from the skin and environment beneath a cast or other orthopedic device to the outside environment where the moisture is removed by evaporation providing a dry atmosphere beneath the cast. The resulting dry environment reduces the ill effects of bacterial, fungal and mildew growth, reduces odor, increases dryness and comfort, and allows the wearer to bathe and swim.

DISCUSSION OF THE BACKGROUND

The treatment of orthopedic injuries, such as bone fractures, usually involves immobilization of a portion of the body in a cast. Immobilization protects the injured body portion, maintains alignment of the bones and prevents further injury. Typical casting materials include plaster of paris or fibers impregnated with plaster of paris as well as newer casting materials such as Fiberglass and polyurethanes which are lightweight and waterproof.

Typically, the injured body portion is wrapped with cotton to provide a cast lining which protects the skin from the cast material itself. The cast lining has a cushioning effect and enables easier removal of the cast after the healing period is complete. Traditionally, cotton or hydrophobic synthetic fabrics have been used as a cast lining.

The use of cotton cast lining has the disadvantage that cotton absorbs and retains moisture and thus becomes soggy. For example, cotton cast lining absorbs perspiration or water introduced under the cast when the casted limb or body portion is immersed in water when swimming or bathing. Typically, the cast lining must be dried through the casting material or, alternatively, the total cast and lining must be removed and replaced, a difficult and time consuming process.

Additionally, cotton fibers are hollow and retain moisture in the cotton fabric; cotton even absorbs and pulls moisture from the air. This moist environment combined with heat generated from the casted body portion enables the growth of mildew and bacteria on the cast lining beneath the protective cast. Mildew and bacterial growth are the source of itching, rashes, unpleasant odor and infections.

Once cotton or a cotton-like liner becomes wet, it may, for all practical purposes, never dry out. This condition leaves the skin in a continual wet or damp state. The skin then starts to breakdown. Since the skin is the body's primary barrier against infection, skin breakdown allows microorganisms, such as bacteria and fungi, to invade the underlying tissue causing the skin and underlying tissue to macerate, i.e., undergo a softening and decomposition. Maceration of the skin can lead to complete loss of the healed condition in cases of a foot cast or serious damage and loss of proportions of the palm in cases of a hand/arm cast. Maceration also leads to local necrosis of the skin and subcutaneous tissues.

Cast liners have also been developed from hydrophobic polymers. U.S. Pat. No. 4,539,982 describes a flexible, odor-adsorbing web in the form of a sheet-like matrix containing open-celled or closed-cell foam or cellulosic fibers in a binder filled with activated carbon particles. The surface of this matrix which is in contact with the skin is a hydrophobic fiber layer which has preferably been needle-punched into the carbon containing matrix. The outer surface of the matrix may include a hydrophilic fiber layer, also needle punched into the foam matrix. In use, perspiration generated at the skin surface is wicked by the hydrophobic fibers into the foam matrix where the activated charcoal particles adsorb odor causing components. The aqueous components of perspiration are absorbed by the hydrophilic fibers and transported through the foam matrix to the space between the cast and the cast lining. This structure is expensive and does not sufficiently remove moisture from beneath the cast and wick the moisture to the outside to dry. It has the further disadvantage of having a hydrophobic fiber layer in contact with the skin causing some discomfort during use.

U.S. Pat. No. 4,516,572 describes a perforated closed-cell padding material for use as a cast lining. The padding material is substantially non-wettable by either water from the surrounding environment or by perspiration. The padding material is permeable to water by virtue of the perforations which allow water vapor transmission through the holes into the atmosphere. The smoothness of the padding material allows trapped water to actually run down and out the end of the cast along the skin. Trapped moisture is transported by the perforations in the padding material when the outside of the cast is heated with a hair dryer, for example. Although an improvement over cotton cast lining, this padding material retains substantial amounts of water unless the cast lining is dried by heating, a time consuming and difficult process as noted above.

Hydrophilic polymers have been used as artificial skin materials and for wound coverings in which a moist environment is maintained around the wound. Wounds resulting in total or partial destruction of the epidermal skin layer such as second and third degrees burns, severe abrasions, ulcers and donor sites for skin grafting are typically covered with these materials in order to keep the wound hydrated and promote healing. These hydrophilic materials adsorb fluids exuded from wounds allowing evaporation of excess moisture while maintaining a generally moist environment around the wound. Such materials are described by U.S. Pat. No. 2,858,830; U.S. Pat. No. 4,554,317 and U.S. Pat. No. 5,098,500.

Hydrophobic cast linings are inferior in their ability to transport moisture from under a cast to the outside environment. Hydrophilic materials which adsorb moisture to maintain a moist environment are unsuitable as cast linings where it is desirable to maintain a dry environment beneath the cast. A need continues to exist, therefore, for improved cast lining materials.

SUMMARY OF THE INVENTION

Accordingly, one object of the present invention is to provide a cast lining which is capable of transporting moisture from beneath a cast to the air within the cast space and also to the outside environment where evaporation may occur. This allows the wearer to swim, shower and bathe since the cast lining will dry in a short time, generally about 4–6 hours. The cast lining of the invention also increases patient comfort and reduces the discomfort of not being able to shower or bathe.

A further object is to provide a cast lining which reduces the growth of mildew, bacteria and fungi on the cast lining beneath the cast thereby reducing itching, rashes and odor and increasing the comfort of the cast. By reducing the continual skin contact with moisture, the chance for maceration and necrosis of the skin is greatly reduced.

These and other objects which become apparent from the following specification have been achieved by the present cast lining which is made from a hydrophilic synthetic polymer fabric. The cast lining of the present invention transports moisture from beneath a cast to the outside atmosphere where the water is evaporated, thereby providing a dry environment beneath the cast. The dryer environment beneath the cast results in less mildew, bacterial and fungal growth and correspondingly less itching, rashes and odor associated with this growth. The drier environment beneath the cast also reduces the occurrence of maceration and necrosis of the skin and underlying tissues beneath the cast.

DESCRIPTION OF THE PREFERRED EMBODIMENTS

Figure 1:
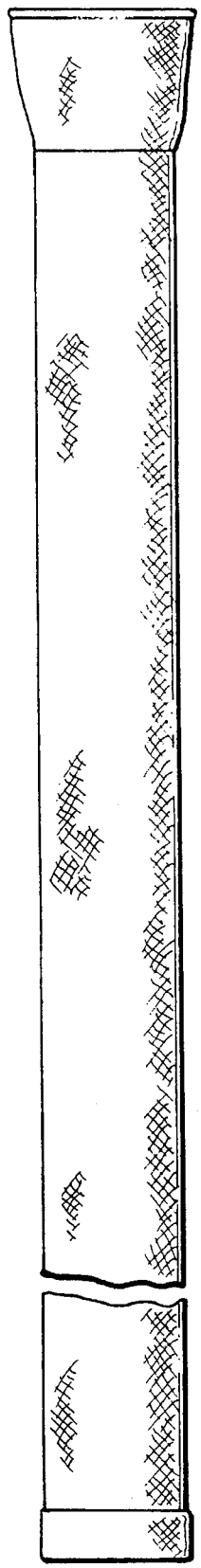
FIG. 1 shows an embodiment of the invention in which the cast lining is a tube having two open ends.
Figure 2:
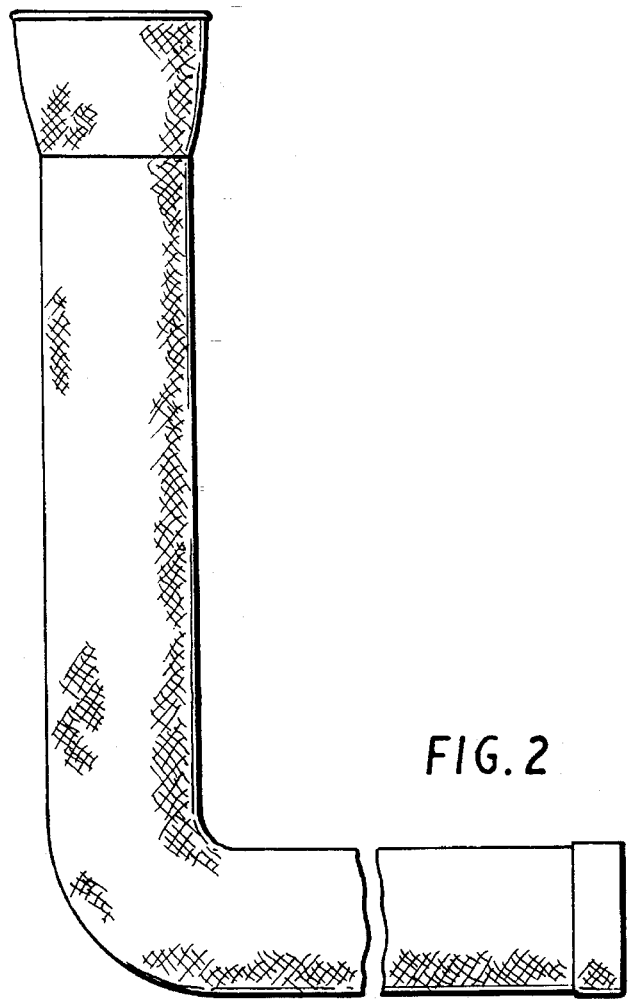
FIG. 2 shows an embodiment of the invention in which the cast lining is a tube having two open ends and a curved portion between the open ends.
Figure 3A:
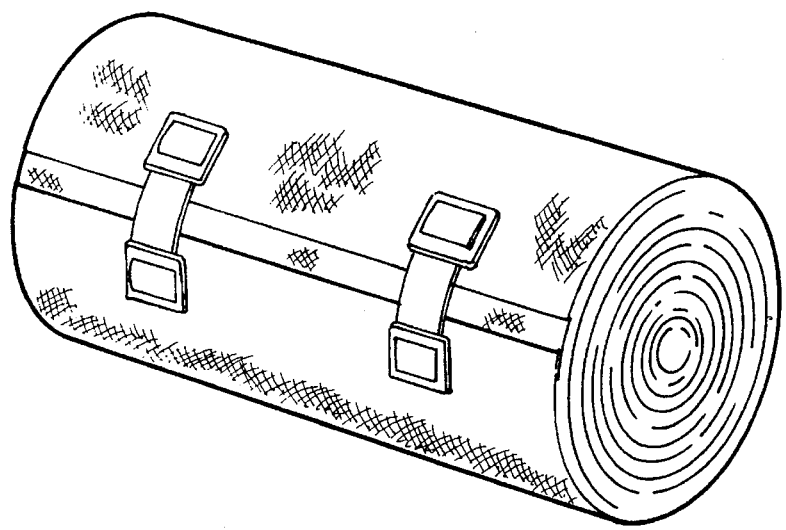
FIG. 3A shows an embodiment of the invention in which the cast lining material is a strip or sheet in the form of a roll.
Figure 3B:
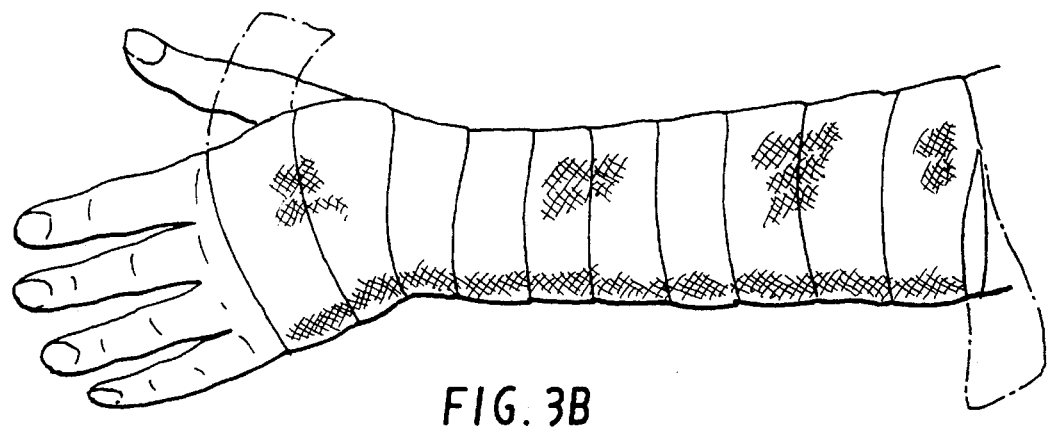
FIG. 3B shows a hand and arm which have been wrapped with the cast lining material shown in FIG. 3A.

Broadly described, the cast lining of the present invention is a fabric article made from hydrophilic synthetic polymer fibers. Generally, the fabric article will be in the form of thin strips, sheets or tubes which are applied to the affected body part by wrapping, layering or sliding onto the body part. For example, the material may be in the form of a roll of continuous fabric strip material having a width generally from about 1–7 inches, preferably 3–5 inches, and an optional length, generally from about 0.5–30 ft., preferably 2–8 ft. When in a sheet form, the fabric cast lining will generally have a width of about 8–36 inches, preferably 12–24 inches, and an optional length, generally from about 1–8 ft., preferably 1.5–6 ft. The material may be applied from the roll by wrapping around the affected area before applying a cast, brace or other orthopedic or prosthetic device.

Alternatively, the fabric may be formed into a tube with or without elastic having open ends using a conventional circular knitting machine, i.e. a hosiery-type machine. In this embodiment, the cast lining is in the form of a continuous tube having two open ends, and will generally having a diameter of about 0.5–8 inches. Tubes having this diameter can be easily fitted over injured body parts, including fingers, wrists, arms and legs before a cast, brace or other orthopedic device is fitted over the injured part. If larger diameter cast lining tubes are desired, two or more smaller cast lining tubes may be cut lengthwise and then sewn or welded together to form a larger diameter cast lining tube. The preferred means for attaching the separate smaller cut cast lining tubes is with a serge stitch, in order to minimize any ridges in contact with the skin and to improve comfort. Other stitches, such as a flat lock stitch may also be used. In this embodiment, from half of a lining tube to 4 lining tubes are generally attached to one another to form the larger diameter cast lining tube.

The construction of the open ends of the cast lining tube is not limited. In the simplest embodiment, the cast lining tube will have the same construction throughout the entire fabric article to the open ends of the tube. However, in other embodiments, the open ends of the tube may be cuffed, fitted with elastic or may be the runout of the circular knitting machine. Conveniently, the cast lining tube has a cuff portion at one end thereof, in which the end portion is folded into or over the tube and stitched to the tube wall. In this embodiment, there is no particular limitation to the end of the cast lining tube which is opposed to the cuff portion. The cast lining is generally fabricated to be substantially longer than is needed to cover the injured body part, and the excess cast lining is cut off after application of the case, brace or other orthopedic device. For example, when the cast lining is used in conjunction with a lower arm cast for treating a broken arm, the cast lining tube is fitted over the injured arm such that an excess portion of the cast lining tube extends to or beyond the fingers. After the cast has been applied to the broken arm, the excess cast lining tube is cut away and/or folded down over the finished cast. It is preferable to have both ends of the tube folded over the cast. The folded cast lining applied in this manner protects the end of the cast, brace or device and provides padding for the injured arm and, more importantly, provides increased surface area for increased evaporation through the hydrophilic wicking action of the cast lining. For this reason, the length and structure of the end portion opposed to the cuff portion are not critical. Conveniently, the end portion opposed to the cuff portion is the runout or end of run from the circular knitting machine.

If desired, the cast lining tube may be constructed with one or more openings or slits to accommodate the body appendages over which the cast lining is applied. Alternatively, the cast lining tube may be cut by the person applying the cast lining to the body part to provide an opening or slit for a body appendage. For example, openings or slits may be used to accommodate thumbs, fingers, toes, elbows, knees, arms, legs, neck, etc. For convenience, the cast lining tube having openings or slits may be in the form of a garment, such as a shirt, underwear, socks, etc., more particularly in the form of t-shirts, panties, briefs, tights including panty hose, leotards, gloves and caps for wear on the head. In this embodiment, the cast lining garment is applied so as to cover the affected body portion. This embodiment of the invention is also effective in treating topical (dermatological) microorganism infections by covering the area of skin affected by the infection with the cast lining material in the absence of broken bones or other need for a cast, brace or orthopedic device. That is, the cast lining material in any form may be used simply to treat topical microorganism infections.

If desired, the cast lining tube may be constructed to have a curved portion between the open end portions. Curved portions are particularly useful to provide a better fit of the cast lining over body portions having joints such as elbows, heels, etc. The curved portions can be conveniently knit into the cast lining on conventional hosiery machines in the same manner in which heel portions are produced in socks.

Alternatively, the curved portions may be sewn in as separate segments or the tubular cast lining may be fitted with a fabric insert having the same or different woven or knitted construction as the cast lining tube. Such inserts allow the cast lining to accommodate swelling which may occur in the injured body part. The insert may be in the form of a ring-shaped annular insert in the tubular cast lining. Alternatively, the insert may have the shape of a regular or irregular polygon having 3–8 sides, that is, the insert may be triangular, square, rectangular, or trapezoidal in shape or even circular. Preferably, the insert is rectangular in shape and oriented longitudinally along the axis of the tubular cast lining. Such inserts may be sewn into the cast lining using any conventional stitch, i.e., a serge or flat stitch. Alternatively, spandex or other rubber elastic can be knit into the tubular cast lining to facilitate a better fit on the injured body part.

The cast lining may be secured by clips, tape or other conventional means if necessary. Multiple layers of the cast lining may be applied. When lining a cast, the plaster or fiberglass/polyurethane casting material is applied over the hydrophilic cast lining.

The cast lining fabric may be non-woven, woven, knitted or a film (substrate) fabric as desired. In a preferred embodiment, the fabric is a stretch knit construction. The tightness of the construction and the thickness of the fabric are not particularly limited and may be adjusted to provide optimum water transport properties. The thickness of the fabric will generally range from about 0.001 to about 1.5 inches, more preferably 0.05–0.30 inch. The yarns are preferably of the size used to make athletic weight socks, e.g. having a fiber denier or equivalent thickness unit of about 0.5–3500 denier, preferably 50–200 denier. The hydrophilic fibers, preferably spun or continuous filament, can be made into fabric using conventional techniques and equipment and no modification of the techniques is required.

The fabric of the invention can be constructed into any fabric from essentially any synthetic fiber or substrate including polyesters, polyolefins, polyamides and acrylics as well as specialty fibers such as NOMEX (an aromatic nylon fiber) and KEVLAR (an aromatic polyamide fiber). Synthetic fibers can be of the continuous filament type, a spun fiber or can be in the form of staples or other non-continuous forms.

The cast lining of the present invention is prepared from hydrophobic synthetic fibers. Since synthetic fibers are hydrophobic, it is necessary to treat the fabric with a treating process which will render the surface of the fabric hydrophilic. Numerous techniques have been suggested for rendering fabrics hydrophilic. Some techniques involve modifying the surface of the fabric to introduce small voids so as to physically trap the aqueous media into the fabric. Other techniques involving chemically modifying the surface of the fabric have been suggested in the patent literature, see for example U.S. Pat. Nos. 3,652,212, 4,242,408, 4,448,839, 4,808,188, 4,081,381 incorporated herein by reference. A polyester fabric under the trade name VISA exhibiting the necessary hydrophilic properties is sold by Milliken & Co., and fabric under the trade name SCOTCH RELEASE is sold by manufacturers using 3M chemicals. Other fibers having hydrophilic properties which may be used in the invention include AKWATEK and AKWADYNE sold by Comfort Technologies, Inc. in which the fibers are treated with lithium cations and borohydride anions. Further, hydrophobic synthetic fibers may be treated with topical hydrophilic wetting agents.

The surface of the hydrophilic fibers may be treated by any suitable molecular, physical or chemical process or combination thereof, to render the fibers hydrophilic. For example, fibers caustically etched with grooves are hydrophilic and transport moisture, and are known in this art. Additionally, fibers having a modified cross-section, i.e., irregular, non-oval, fluted or grooved fibers are known hydrophilic fibers and may be used to prepare the cast lining of the present invention. Copolymer fibers prepared by combining the extrusion of synthetic fibers and fibers containing absorbing components such as poly(ethylene glycol) are acceptable for use in the present invention. Examples of the fibers described above are commercially available under the tradenames COOLMAX by DuPont (non-oval fiber) and HYDROPHIL by Allied (copolymer extrusion with poly(ethylene glycol) fibers). Hollow synthetic fibers are hydrophilic and are capable of transporting water through the capillary fibers. Such hollow fibers are known in this art and available commercially, for example, as THERMAX fibers from DuPont.

The cast lining fabric of the invention may also be prepared from a blend of the hydrophilic synthetic fiber and a second fiber which is different than the hydrophilic fiber, so long as the fabric retains hydrophilic properties. For example, a blend of about 100–5% by weight, preferably 90–50% by weight, of a hydrophilic synthetic fiber and about 0–95% by weight, preferably 10–50% by weight, of a conventional hydrophobic fiber or cellulosic fiber, such as cotton, may be used to prepare the fabric cast lining of the invention.

Hydrophobic fibers such as nylon and polyester which have been rendered hydrophilic by chemical surface treatment are particularly preferred for manufacturing the cast lining of the present invention. Suitable chemical processes are described, for example, in U.S. Pat. No. 4,705,831; U.S. Pat. No. 4,726,968; U.S. Pat. No. 4,743,267; U.S. Pat. No. 4,672,005; U.S. Pat. No. 4,790,907; U.S. Pat. No. 4,563,507; U.S. Pat. No. 4,806,125; and U.S. Pat. No. 5,154,727. These patents are incorporated herein by reference for a more complete description of suitable chemical modification processes and synthetic hydrophilic fabrics which are prepared using these processes. This type of hydrophilic fiber is commercially available under the tradename INTERA from Intera Corporation. Treatment of the hydrophobic fibers to chemically modify the surface thereof has the additional advantage of minimizing or preventing the treated fibers from unraveling when fabricated into a cast lining article, for example a cast lining tube.

In a particularly preferred process, the hydrophobic synthetic polymer fiber substrate is contacted with an aqueous mixture containing a water-soluble vinyl monomer and a hydrophobic vinyl monomer at a temperature of between about 40°–100° C. Polymerization of the water-soluble monomer is then initiated by a chemical or physical initiator to form a vinyl polymer evenly disposed on the substrate fiber. Suitable water-soluble vinyl monomers and hydrophobic monomers are described in U.S. Pat. No. 4,672,005.

The cast lining article of the present invention may be constructed to contain elastic fibers or strands so that the cast lining is elastic and thereby conforms more closely to the injured part. Any conventional elastic which can be used with fabric may be used in the cast lining of the present invention. Suitable elastic is commercially available, for example, spandex (LYCRA) is a rubber elastic which is produced by DuPont Co. The elastic fibers are generally interwoven with the fibers of the cast lining. However, the elastic may be simply stitched to the surface of the cast lining. When the cast lining is in the form of a roll of strip material and contains elastic, the cast lining will be in the form of a hydrophilic elastic bandage.

The cast lining of the present invention is preferably prepared from solid synthetic hydrophilic fibers. Such fibers are not hollow and, therefore, do not absorb and retain moisture in the manner in which cotton and foam products absorb water. Rather, it is believed that the hydrophilic synthetic fibers which comprise the fabric cast lining of the present invention adsorb water at the surface of the fiber and transport the adsorbed water along the length of the fibers. Water (moisture) is transported away from the skin and along the hydrophilic fabric to the end of the cast where evaporation removes water to the atmosphere. The surface of the skin in contact with the cast lining is, therefore, in contact with a hydrophilic polymer fabric and not a hydrophobic polymer fabric or sheet as in prior cast linings. In contrast to cotton and cellulosic materials which swell and hold moisture, the cast lining of the invention transports moisture to the atmosphere providing a dry and comfortable feeling for the cast wearer. The adsorptive fabric of the present invention is superior to the prior absorptive materials in its ability to spread moisture over the surface of the fibers resulting in more efficient moisture transport and faster evaporation from the exposed ends of the cast and to the air within the cast space. Faster moisture transport and faster evaporation result in more efficient moisture transport and, therefore, reduced moisture trapped beneath the cast. The reduced moisture levels in the cast lining and against the skin of the affected body portion result in lower levels of mildew, bacterial and fungal growth and thereby increased dryness and comfort, lower levels of itching, rashes and odor, and further allow swimming and bathing.

The hydrophilic synthetic fiber fabric cast lining of the present invention should effectively transport moisture. Preferably, the hydrophilic fiber should wick water at a rate of at least 1/10 inch per initial min., more preferably at least ½ inch per initial min. in a standard wicking test, for example the standard TDI No. 4 (Textile Distributors Institute) test or the vertical wicking test described below. Hydrophilic fabrics suitable for use in the present invention can be readily determined by one having ordinary skill in this art.

Vertical wicking of hydrophilic fabrics which may be used in the present invention can be determined by the following procedure. A piece of fabric measuring 1×6 inches is cut from the bulk hydrophilic fabric. A non-indelible ink line is drawn vertically through the middle of the fabrics such that the path of transported water is more visible. The fabric is held vertically and immersed to a depth of ½ inch in a 200 milliliter beaker containing 150 milliliters of water. After one minute of elapsed time, the vertical distance traveled by the transported water is measured.

The present invention also provides a method for preparing an orthopedic cast from conventional cast materials such as plaster of paris (calcium sulfate hemihydrate) and fiberglass/polyurethane having an inside lining (layer) of the cast lining material of the present invention. In this method, one applies the cast lining article of the present invention over the outer surface of a body portion in need of an orthopedic cast. Casting material is then applied to the exposed surface of the cast lining material and the casting material is hardened. During application of the casting material to the cast liner, a portion of the casting material penetrates the cast lining material. When the cast lining material hardens, a cast having an inner layer of the cast lining material of the present invention is formed where the inside lining is physically attached to the cast lining material forming the orthopedic cast. The cast so formed is also within the scope of the present invention.

An additional use for the cast lining material of the present invention is in the treatment of exudative skin rashes, eruptions, lesions, etc. The cast lining article transports moisture of the exudate away from the skin thereby keeping the skin area of the rash, eruption or lesion dry, thereby promoting healing. The cast lining article also protects the skin area covered by the article and functions to limit spread of the rash and reduce itching. The cast lining article of the present invention when used in this manner is generally applied directly to the affected skin area without a cast, brace or orthopedic device. If necessary, conventional clips or fasteners may be used to hold the cast lining material in place. The use of a tubular cast lining material generally obviates the need to use extraneous clips or fasteners.

The cast lining of the present invention can be used to treat any exudative dermatitis. The cast lining is particularly effective in reducing the spread and itching of toxicodermatitis, i.e., the inflammation of the skin due to the action of a contact poison or toxin. In this embodiment, the cast lining is particularly effective in treating contact dermatitis, in particular, contact dermatitis associated with plants of the genus Toxicodendron, including poison ivy (*T. radicans*), poison oak (*T. diversilobum*), and poison sumac (*T. vernix*).

A further use of the cast lining material of the present invention is a method of treating a topical microorganism infection. In this embodiment, the area of skin affected by the microorganism infection is covered with the cast lining material of the present invention. This embodiment is suitable for treating fungal, bacterial and mold infections of the skin. While not being bound by an particular theory, it is believed that the cast lining material of the present invention exhibits a growth limiting effect on fungi, bacteria and mold by depriving these microorganisms of essential moisture necessary for microorganism growth. In this embodiment, the material of the present invention may have any form discussed above, including a strip, sheet, tube with open ends or garment. This method is suitable for treating topical infections without the further application of an orthopedic device such as a cast or brace. Specific microorganism infections contemplated within the scope of the present invention include infections by organisms of the genera Tinea and Candida. Specific infections include jock itch (*Tinea cruris*), athlete's foot (*Tinea pedis*) and vaginitis (*Candida albicans*).

Other features of the invention will become apparent in the following description of an exemplary embodiment which is given for illustration of the invention and is not intended to be limiting thereof.

EXAMPLE

A cast lining tube 30 inches long having a 1×1 ribbed knit construction and having a diameter of about 3 inches was prepared on a conventional hosiery-type circular knitting machine C108 needle with a 3.75 inch cylinder. The cast lining tube was knit from 97 wt. % polyester fibers and 3 wt. % spandex elastic. The backing yarn (12 wt. % of the cast lining article polyester) was made of 1/150 denier polyester. The facing yarn (88 wt. % of the cast lining article polyester) was made of 1/6 spun polyester. The knit cast lining tube prepared in this manner was finished by rendering the surface hydrophilic according to the method described in U.S. Pat. No. 4,672,005.

The cast lining tube preparation as described above was laid adjacent to the arm of an adult male volunteer and aligned with the mid-triceps area of the arm. Using scissors, a quarter inch slit was made in the side of the cast lining adjacent to the thumb in order to provide a thumb hole. The cast liner was then slid over the arm until the thumb extended through the thumb hole. A fiberglass cast material was then applied over the cast lining and allowed to harden. The cast lining material extending beyond the fingers was removed by cutting and the cast lining covering the fingers was then folded over the end of the fiberglass cast material in the region of the thumb.

The casted arm was then submerged in water, removed and allowed to dry. The cast lining was substantially dry in about four hours.

The cast was then removed with a conventional cast saw and the cast lining removed after cutting with scissors.

Obviously, numerous modifications and variations of the present invention are possible in light of the above teachings. It is, therefore, to be understood that within the scope of the appended claims, the invention may be practiced otherwise than as specifically described herein.

What is claimed as new and is desired to be secured by letters patent of the United States is:

1. A cast lining material for use beneath an orthopedic cast, said material consisting essentially of a hydrophilic synthetic fiber material in the form of a fabric.

2. The lining fabric of claim 1, wherein said material is in the form of a strip, tube or sheet.

3. The lining fabric of claim 2, wherein said material is in the form of a tube having two open ends.

4. The lining fabric of claim 3, wherein said material has a curved portion between said open ends.

5. The lining fabric of claim 3, wherein said material is a knitted tubular fabric.

6. The lining material of claim 1, having a thickness of about 0.001 to about 1.5 inches.

7. The lining material of claim 1, wherein said fiber has a diameter of about 0.5–3500 denier or equivalent thereof.

8. A cast lining material for use beneath an orthopedic cast, said material being in the form of a fabric and consisting essentially of a blend of elastic fibers and a hydrophobic synthetic fiber material.

9. The lining fabric of claim 1, wherein said material is a continuous strip material having a width of about 1–7 inches and a length of about 0.5–30 ft.

10. The lining fabric of claim 1, wherein said material is made hydrophilic by contacting a synthetic material with an aqueous mixture containing a water-soluble vinyl monomer and a hydrophobic vinyl monomer at a temperature between about 40°–100° C. and then initiating polymerization of the monomers to form a polymer disposed on the material surface.

11. The lining fabric of claim 1, wherein said material is in the form of a garment.

12. The lining material of claim 11, wherein said garment is selected from the group consisting of shirts, socks, panties, briefs, tights, panty hose, leotards, gloves and caps.

13. The lining fabric of claim 1, wherein said material wicks water at a rate of at least 1/10 inch per initial minute in a vertical wicking test.

14. A cast lining material for use beneath an orthopedic cast, said material being in the form of a fabric and consisting essentially of a blend of a hydrophobic synthetic fiber and a second fiber which is different than said hydrophobic synthetic fiber.

15. The lining fabric of claim 1, wherein said material is comprised of fibers having grooves etched therein.

16. The lining fabric of claim 1, wherein said material is comprised on fibers which are irregular, non-oval or fluted in cross-section.

17. An orthopedic cast for support of a body portion in need thereof, comprising a rigid cast material having an inner surface lining, wherein said lining consists essentially of a hydrophilic synthetic fiber material in the form of a fabric.

18. A method of preparing an orthopedic cast for support of a body portion in need thereof, comprising the steps of:
(a) covering a body portion in need of an orthopedic cast with a cast lining material, wherein said cast lining material consists essentially of a hydrophilic synthetic fiber material in the form of a fabric,
(b) applying orthopedic cast material to said body portion covered with said cast lining material, and
(c) hardening said orthopedic cast material to form an orthopedic cast having a lining of said cast lining material.

19. The method of claim 18, wherein said fabric is a blend of a hydrophilic synthetic fiber and a second fiber which is different than said hydrophilic synthetic fiber.

20. A method of transporting moisture from beneath an orthopedic cast applied to a body portion, comprising applying a cast lining material to the body portion before applying the orthopedic cast, wherein said cast lining material consists essentially of a hydrophilic synthetic fiber material in the form of a fabric, whereby moisture formed beneath the orthopedic cast is transported by said cast lining material to the edge of said cast and to the air within the cast and evaporated.

21. The method of claim 20, wherein said cast lining material is in the form of a strip, tube or sheet.

22. The method of claim 20, wherein said cast lining material is in the form of a tube having two open ends.

23. The method of claim 20, wherein said cast lining material is in the form of a garment.

24. The method of claim 23, wherein said garment is selected from the group consisting of shirts, socks, panties, briefs, tights, panty hose, leotards, gloves and caps.

25. The method of claim 20, wherein said fabric is a blend of a hydrophilic synthetic fiber and a second fiber which is different than said hydrophilic synthetic fiber.

* * * * *